United States Patent
Lambert et al.

(10) Patent No.: US 7,295,295 B2
(45) Date of Patent: Nov. 13, 2007

(54) PASTE SOLIDS MEASUREMENT IN REAL TIME

(75) Inventors: Georgia Lynn Lambert, La Porte, TX (US); Dalia I. Diaz, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 360 days.

(21) Appl. No.: 11/010,719

(22) Filed: Dec. 13, 2004

(65) Prior Publication Data

US 2006/0128878 A1    Jun. 15, 2006

(51) Int. Cl.
*G01N 21/41* (2006.01)
(52) U.S. Cl. .................................... 356/128
(58) Field of Classification Search ............... None
See application file for complete search history.

(56) References Cited

U.S. PATENT DOCUMENTS

| | | | | |
|---|---|---|---|---|
| 2,864,784 A | * | 12/1958 | Marks | 524/308 |
| 3,526,771 A | * | 9/1970 | Henkel et al. | 250/565 |
| 3,999,857 A | * | 12/1976 | David et al. | 356/133 |
| 4,980,065 A | * | 12/1990 | Hsu | 210/632 |
| 5,311,274 A | * | 5/1994 | Cole, Jr. | 356/133 |
| 5,396,325 A | * | 3/1995 | Carome et al. | 356/128 |
| 5,870,185 A | * | 2/1999 | See et al. | 356/128 |
| 7,016,026 B2 | * | 3/2006 | DiFoggio et al. | 356/128 |
| 2004/0145731 A1 | * | 7/2004 | Nakajima et al. | 356/135 |

OTHER PUBLICATIONS

Finch, C.A., ed. Polyvinyl Alcohol Developments. Wiley, 1992.*

* cited by examiner

*Primary Examiner*—Gregory Toatley, Jr.
*Assistant Examiner*—Jonathan Skovholt
(74) *Attorney, Agent, or Firm*—M. Susan Spiering

(57) ABSTRACT

A real-time method of determining paste solids includes: correlating the refractive index of a paste with solute concentration in a solvent using a plurality of paste solids concentrations, typically including at least two paste solids concentrations greater than about 5 percent; submersing a fiber optic refractometer sensor into a sample and allowing it to equilibrate for a period of from about 30 seconds to about 20 minutes prior to measuring refractive index of the sample; measuring the refractive index of the paste sample with the fiber optic refractometer sensor; and determining the concentration of solute in the sample using the correlation.

33 Claims, 3 Drawing Sheets

PASTE SOLIDS MEASUREMENT IN REAL TIME

This present invention relates to a novel methodology for determining paste solids in viscous pastes. The method is rapid and can be used in-line or on sampled material, requiring no sample preparation. A preferred technique utilizes a digital fiber optic refractometer which is calibrated and programmed to output concentration directly. The technique is more accurate, reproducible and less time-consuming than the standard gravimetric techniques known in the art.

BACKGROUND OF THE INVENTION

Paste solids are measured in connection with monomer and polymer manufacture in order to control the processes and characterize product which is sold in intermediate or finished form. Known techniques are gravimetric in nature and are difficult to reproduce especially if a relatively volatile solvent such as methanol is used as is the case in connection with processing vinyl acetate monomer into polyvinyl alcohol. Conventional techniques involve baking a paste sample in an oven at 150° C. or so to drive off the solvent.

Numerous types of optical sensors sensitive to changes in refractive index have been described in the art. These include devices which operate by measuring optical energy internally reflected at an interface with a surrounding medium. Optical fibers may serve to direct light onto the interface and may also serve as the optical detectors themselves. These devices are relatively inexpensive to produce, immune from electromagnetic interference and intrinsically safe in explosive environments.

A fiber optic refractometer does not require light to pass through the process liquid, but offers a means of continuously measuring RI values. The efficiency with which optical fibers transmit light is determined by the disparity of RI that exists between the core and cladding materials. It follows that such a device could be used as a refractometer if the process liquid of interest became the "cladding" about a glass core. By measuring the efficiency at which such a fiber transmitted light energy, the RI of the liquid cladding could be determined. The concept of attenuated total reflectance (ATR) forms this category of fiber optic refractometers. (See Kapany, N. S., and J. N. Pike, "Fiber Optics, part IV, a photorefractometer," Journal of the Optical Society of America, vol. 47, no. 12, 1957, pp. 1109-1117.) In these instruments, a conical beam of light with a uniform intensity, I watts/steradian, excites a glass rod or fiber. The transmitted light is then measured by a photosensitive device.

A variation of the ATR fiber optic refractometer uses a laser beam incident on the end of the glass rod. (See David, et al., "Design, development and performance of a fiber optics refractometer: Application to HPLC," Review of Scientific Instruments, vol. 47, no. 9, 1976, pp. 989-997; also, U.S. Pat. No. 3,999,857, J. D. David, D. A. Shaw & H. C. Tucker, "Refractive Index Detector," 1976.) The beam angle into the rod is adjusted via a mirror moved by a micrometer until the edge of the "cone of acceptance" (i.e., the numerical aperture or NA) is found. Multiple reflections of the light propagating down the fiber make the transition very sharp. The micrometer reading correlates to the NA, and n.sub.1 can be calculated from equation (4a). The instrument locates the sharp light transition at the edge of the NA, but its output drops to a low, constant level once the incident beam angle exceeds the NA.

Fiber optic refractometers based on Fresnel's equations have also been designed. (See Meyer, M. S., and G. L. Eesley, "Optical Fiber Refractometer," Review of Scientific Instruments, vol. 58, no. 11, 1987, pp. 2047-2048.) Monochromatic light is transmitted down a single mode fiber and reflects off the far end of the fiber, immersed in the process liquid. The core at that end of the fiber is polished smooth, perpendicular to the fiber axis. Fresnel reflections from the core/liquid dielectric interface are transmitted back through the fiber to a photo sensor.

Fiber optic refractometers using bent fibers have also been developed. (See Golunski, W., et al., "Optical fiber refractometer for liquid refractive index measurement," Proceedings of the SPIE—Optical Fibers and Their Applications V, vol. 1085, 1990, pp. 473-475.)

U.S. Pat. No. 5,311,274 to Charles F. Cole Jr., May 10, 1994, describes an ATR type fiber optic refractometer suitable for use in determining on-line measurements of the hydrogenation state of edible oils during a partial hydrogenation process. This refractometer does not require light to pass through the process fluid and is therefore unaffected by the presence of light diffusing particulate matter in the process fluid.

U.S. Pat. No. 5,396,325 assigned to the Mercury Iron and Steel Company, Mar. 7, 1995, describes a refractometer of the fiber-optic Fresnel "reflectance" type suitable for measuring refractive index provided with a sensor element and first and second optical fibers coupled to the sensor element. Optical energy incident at an angle to a surface less than the critical angle is governed by the Fresnel reflectance equation:

$$R = 1/2 \left( \frac{\sin^2(\theta_i - \theta_r)}{\sin^2(\theta_i + \theta_r)} + \frac{\tan^2(\theta_i - \theta_r)}{\tan^2(\theta_i + \theta_r)} \right)$$

where $\theta_i$ is the angle of incidence of the optical energy and $\theta_r$ is the angle of the refracted optical energy. At a specific angle of incidence, if the refractive index of the covering medium approaches the refractive index of the glass layer, the percent of reflectance decreases and more optical energy passes into the covering medium. Since the change in the reflected optical energy is dependent on changes in the angle of incidence and the refractive index of the covering medium, the above equation may be used as the basis of a detection scheme.

While fiber optic refractometers have been used for measuring concentration, such as protein concentration in dilute agitated aqueous solutions; it is conventionally believed that a fiber optic probe would not function well when submersed in viscous paste, due to air bubbles and an inability to circulate fluid about the probe.

It was unexpectedly found in accordance with the present invention that concentrated solutions or pastes are amenable to concentration measurement by way of a calibrated refractometer. The method provides essentially real time concentration measurement as opposed to gravimetric techniques which can take an hour or more. The method is also more accurate since a major source of error, unaccounted for evaporation, is minimized.

SUMMARY OF THE INVENTION

In accordance with the present invention, it has been found that a digital fiber optic refractometer can be utilized to determine real time paste solids in high solids streams by direct insertion into the stream or sample. The method is particularly suited for determining the paste solids in vinyl acetate/methanol systems. The method is a direct measurement and does not involve lengthy sample preparation. By utilizing this inventive method, significant reduction times in running paste solids were achieved. By using this instrument, running times of 1 hour or more per sample were reduced to less than 5 minutes per sample, with greater accuracy and reproducibility. The method is also used to characterize solids content of a polyvinyl alcohol aqueous solution or a paste at relatively high concentrations without the need for added reagents such as flocculants and so forth. The method can reduce the time needed to make a solution or paste by reducing the time needed to accurately assay its solid content.

One aspect of the invention is thus a method for preparing and characterizing a composition comprising: a) preparing a composition selected from the group consisting of: i) viscous pastes having at least 5% W/W solids; or ii) aqueous solutions of polyvinyl alcohol, wherein the polyvinyl alcohol resin has a characteristic viscosity of from about 2 to about 60 cps at 20° C. and a concentration of 4% by weight; b) calibrating a fiber optic refractometer to measure solids concentration of the composition of step a); and c) measuring the solids concentration of the composition of step a) using the calibrated refractometer. Typically, an aqueous solution of polyvinyl alcohol is prepared by dispersing particulate polyvinyl alcohol in water and cooking the mixture at a temperature between about 140° F. and 205° F. for at least about 20 minutes and the polyvinyl alcohol solution has a viscosity of from about 2 cps to about 10,000 cps at 20° C. In most cases the polyvinyl alcohol solution has a concentration of from about 4 percent to about 25 percent by weight polyvinyl alcohol resin.

There is provided in another aspect of the present invention a method of determining solids in a viscous paste having a concentration of greater than 5 percent solute W/W with solvent including the steps of: correlating the refractive index of a paste with solute concentration in a solvent using a plurality of paste concentrations, including at least two paste concentrations greater than about 5 percent; measuring the refractive index of a paste sample with a fiber optic refractometer sensor; and determining the concentration of solute in the sample using the correlation of step (a). The solvent may include methanol or water, while the solute comprises vinyl acetate monomer in a preferred embodiment. In other applications, the solute has a component selected from vinyl acetate oligomers and vinyl acetate polymers. The method is advantageously applied to paste samples having a solute concentration of at least about 20 percent, or to paste samples having a solute concentration of at least about 30 percent, or to paste samples having a solute concentration of at least about 40 percent. Generally, the paste sample has a viscosity of at least 2500 cps; usually, the paste sample has a viscosity of at least 5000 or 10,000 cps or the paste sample has a viscosity of about 25,000 cps or more, suitably in the range of 50,000 cps to 100,000 cps. From about 65,000 cps to about 90,000 cps is somewhat typical of production samples, while the correlation may be developed on specimens ranging in viscosity from about 25,000 cps to about 100,000 cps.

Typically, the step of correlating the refractive index of a paste with concentration includes measuring the refractive index of at least two solutions with a fiber optic refractometer sensor. In one preferred case, the fiber optic refractometer sensor is coupled to an optical energy source for supplying optical energy by way of a first optical fiber and the sensor includes an element including a material transparent to at least a portion of such optical energy defining a planar light incident and a planar measuring surface; the first optical fiber connecting the optical energy source and the element for transmitting such optical energy through the element obliquely toward the measuring surface, the first optical fiber also being optically coupled to said element; and wherein the measuring surface is coupled to a photodetector communicating with the element by way of a second optical fiber in a line of reflection of such optical energy from the measuring surface for measuring a multitude of discrete changes in an intensity of optical energy transmitted through the element away from the measuring surface, and being operative to generate a signal that is a function of the measured changes in said intensity. Preferably, the optical sensor includes a temperature sensor so that the correlation can be developed at a first temperature and utilized at a second temperature. For example, the correlation can be developed with specimens at 20° C. to 30° C. and used on samples at 30° C. up to perhaps 60° C., suitably between about 35° C. and 40° C.

Another preferred embodiment provides a method of determining solids in a viscous paste having a concentration of greater than 5 percent solute W/W with solvent comprising: correlating the refractive index of a paste with solute concentration in a solvent using a plurality of paste concentrations, including at least two paste concentrations greater than about 5 percent; submersing a fiber optic refractometer sensor into a sample and allowing it to equilibrate for a period of from about 30 seconds to about 20 minutes prior to measuring refractive index of the sample; measuring the refractive index of the paste sample with a fiber optic refractometer sensor; and determining the concentration of solute in the sample using the correlation of step (a). Typically, the refractometer sensor is allowed to equilibrate for at least about 1 minute prior to measuring the refractive index of the sample; preferably, the refractometer sensor is allowed to equilibrate for at least about 2 minutes prior to measuring the refractive index of the sample; while in still other applications the refractometer sensor is allowed to equilibrate for at least about 4 minutes prior to measuring the refractive index of the sample.

Still other aspects of the invention is improved production processes for converting vinyl acetate to polyvinyl alcohol including the steps of measuring the concentration of a vinyl acetate paste and adjusting concentration in response to the measurement, the improvements generally comprising: correlating the refractive index of a vinyl acetate paste with solute concentration in a solvent using a plurality of paste concentrations, including at least two paste concentrations greater than about 5 percent; measuring the refractive index of a paste sample with a fiber optic refractometer sensor; determining the concentration of solute in the sample using the correlation of step (a); and adjusting the concentration of the vinyl acetate paste in response to the determination of step (c). The measurement technique can also be used to adjust the acid/caustic ratio during saponification.

Still other aspects and advantages will become apparent from the discussions which follow.

BRIEF DESCRIPTION OF DRAWINGS

The invention is described in detail below in connection with numerous Examples and with reference to the appended Figures. In the Figures.

DETAILED DESCRIPTION OF THE INVENTION

Figure 1:
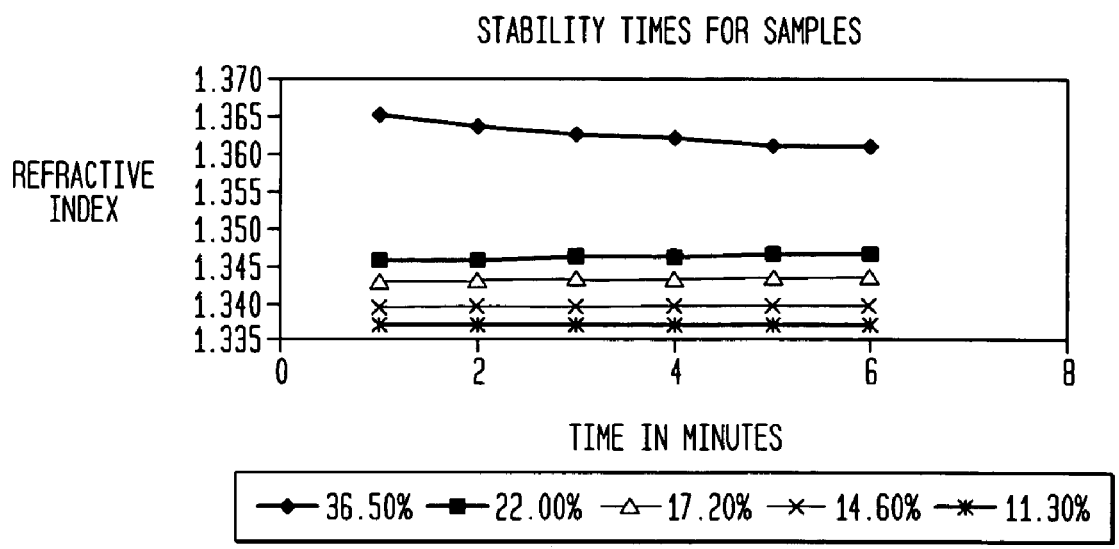
FIG. 1 is a plot of Refractive Index measurement vs. time illustrating sensor equilibration time in various samples.

The invention is described in detail below with reference to various examples for purposes of illustration, only. Modification to particular embodiments within the spirit and scope of the invention, set forth in appended claims, will be readily apparent to those of skill in the art.

As used herein, terminology has its ordinary meaning unless a more specific or more general meaning is given below or is clear from the context.

Centipoise means a unit of the measure of viscosity equal to 1/100 poise. The viscosity of water at 20° C. is approximately 1 centipose.

"Cps" means centipoises, as defined above. Unless otherwise sated, viscosity is measured at 20° C.

"Characteristic viscosity" of a PVOH resin is measured in 4% w/w aqueous solution at 20° C.

"Paste" means a relatively viscous medium, having a viscosity of at least about 100 times that of water, that is at least 100 cps at 20° C.

Refractive index means the ratio of the velocity of light in a vacuum to the velocity of light in a specific material. The higher the number, the slower the speed of the lightwaves in the material.

"RI" means refractive index as defined above.

Vinyl acetate paste means a Paste including vinyl acetate monomer, vinyl acetate oligomers or vinyl acetate polymer or derivatives thereof.

As used herein, the terminology "polyvinyl alcohol resin", "PVOH" and the like refer to resins that are predominately (more than 50 mole %) based on vinyl acetate monomer which is polymerized and subsequently hydrolyzed to polyvinyl alcohol. The degree of hydrolysis refers to the mole % of the resin's vinyl acetate monomer content that has been hydrolyzed. The polyvinyl alcohol resins may be based on vinyl acetate homopolymer or copolymers of vinyl acetate with any suitable comonomer and/or blends thereof. After polymerization, the polymer's vinyl acetate residue is hydrolyzed to polyvinyl alcohol. Comonomers may be present from about 0.1 to 10 mole % with vinyl acetate and include acrylic comonomers such as 2-acrylamido-2-methyl propane sulfonic acid or salts thereof. Other suitable comonomers include glycol comonomers, versatate comonomers, maleic or lactic acid comonomers, itaconic acid comonomers and so forth. Vinyl versatate including alkyl groups (veova) comonomers may likewise be useful. See Finch et al., *Ed. Polyvinyl Alcohol Developments* (Wiley 1992), pp. 84 and following. The comonomers may be grafted or co-polymerized with vinyl acetate as part of the backbone. Likewise, homopolymers may be blended with copolymers, if so desired.

Vinyl acetate paste solids are currently analyzed using a pan solids measurement. This method yields less than favorable accuracy and reproducibility. The error introduced by the evaporation of methanol, during the initial weighing step, is the major contributor to the error in the measurement. Analysis using this test method takes approximately 1-1½ hours. By substituting the use of a fiber optic probe, the measurement variability is greatly reduced. The total measurement time is also cut down to 2-5 minutes. This measurement device can also be used in an in-line application. A particularly suitable device with a submersible fiber optic sensor is a Model 401 Fiber Optic Refractometer available from The Mercury Iron and Steel Co., Cleveland, Ohio.

In order to effectively use the probe, a set of serial dilutions made from paste samples is prepared and analyzed. This is the standard calibration curve generated under ambient conditions. This calibration curve can be installed into a standard refractometer memory at the manufacturer to give % solids results directly rather than a refractive index result.

A series of two calibration curves were created to demonstrate the usefulness of this method. In order to allow for thermal equilibration and the elimination of bubbles and so forth, the refractive index was taken at times of 1 min, 2 min, 3 min, 4 min, and 5 minutes to determine the necessary time for probe quilibration. Results are seen in FIG. 1. The refractive index was then taken 5 different times on 5 different vinyl acetate paste samples to determine the variation between readings.

A concentrated high viscosity paste sample was obtained and 2 diluted sets of 5 serial dilutions was prepared and analyzed by both methods. Several different plant paste samples, ranging in viscosity were then analyzed by both methods to determine the % difference between the measurements systems.

Stability for all samples was reached at about 5 minutes after insertion into sample. The time to stabilize is increased by the increasing paste solids. This is seen in FIG. 1 on the high viscosity paste sample.

A series of repeat measurements were then made, running each sample 5 different times. The sample stabilization time was picked at 2 minutes. Following is the resulting data:

TABLE 1

Reproducibility Data

|  | 1A | 1B | 1C | 1D | 1E |
|---|---|---|---|---|---|
| Mean | 1.3630 | 1.3460 | 1.3431 | 1.3398 | 1.3368 |
| Standard Error | 0.0006 | 0.0004 | 0.0003 | 0.0001 | 0.0001 |
| Median | 1.3635 | 1.3460 | 1.3430 | 1.3400 | 1.3370 |
| Standard Deviation | 0.0013 | 0.0008 | 0.0007 | 0.0003 | 0.0003 |

The standard deviation of these numbers is unexpectedly low with respect to conventional test procedures. It should be noted here that the error that is introduced by the reproducibility of the instrument is 0.0005. This equated to a +/− of 0.004% in the final solids number.

Figure 2:
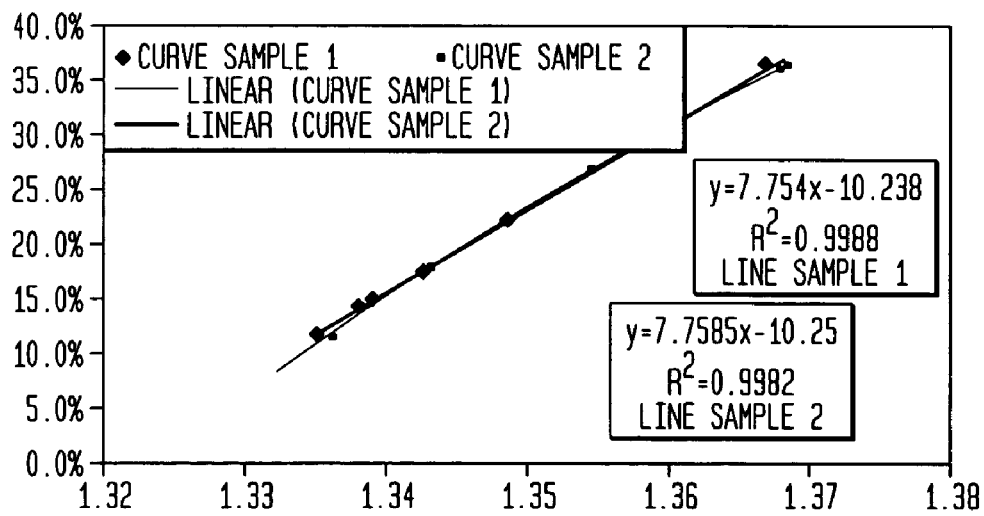
FIG. 2 contains plots of Vinyl Acetate Concentration in Methanol vs. Refractive Index useful as linear calibration curves for a fiber optic refractometer.

The calibration curves were created using two different 5-point lines, and plotting them against themselves to determine the reproducibility of both lines. The results are shown in FIG. 2.

To test the calibration, samples from various viscosities and paste types were obtained and analyzed by using both methods. The results are as follows.

TABLE 2

Comparison of Results
Fiber Optic RI data

| Sample # | RI | Theoretical Solids | Pan Solids | % Difference |
|---|---|---|---|---|
| 1 | 1.3915 | 54.88 | 53.75 | 2.08 |
| 2 | 1.3715 | 39.37 | 39.73 | 0.91 |
| 3 | 1.3695 | 37.82 | 37.57 | 0.66 |
| 4 | 1.3685 | 37.04 | 35.48 | 4.31 |
| 5 | 1.3605 | 30.84 | 30.98 | 0.46 |
| 5 Dupl. | 1.3605 | 30.84 | 31.15 | 1.01 |
| 5 Trip | 1.3605 | 30.84 | 31.11 | 0.88 |

Variation in the number 4 sample can be explained by sample overflow on the pan while in the oven. While qualifying this method, we are using a pan solids method that has been proven to be less than accurate for this type of application. The steady readings obtained with the fiber optic probe prove to be more stable and much quicker than the 1-hour pan solids measurement.

Figure 3:
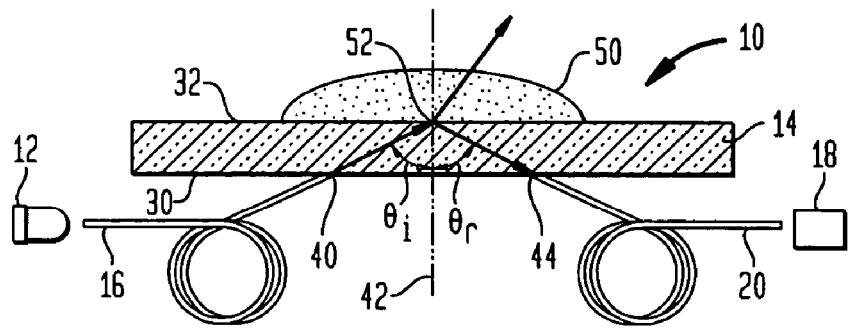
FIG. 3 is a schematic diagram of an optical sensor useful with the invention.

While any suitable refractometer may be employed with the present invention, a refractometer of the Fresnel type described above (See U.S. Pat. No. 5,396,325 to Carome et al.) is one preferred type of refractometer, shown schematically in FIGS. 3-5. Shown in FIG. 3 is an optical sensor 10 including a light-emitting diode ["LED"] optical energy source 12 coupled to an element 14 by means of a first large-diameter-core multimode optical fiber 16 and a photodetector 18 coupled to the element 14 by means of a second large-diameter-core multimode optical fiber 20. The element 14 is in the form of a thin glass plate having a planar light-incident surface 30 parallel to a planar measuring surface 32. The optical fiber 16 is fixed to the light-incident surface 30 at the position 40 so that optical energy transmitted from the optical energy source 12 through the fiber 16 is directed through the element 14 at an oblique angle to the measuring surface 32. The optical fiber 20 is fixed to the light-incident surface 30 of the element 14 at position 44 in the same plane as the optical fiber 16 to receive a sample of optical energy transmitted through the element 14 away from the measuring surface 32.

The term "optical energy" is used to emphasize that the preferred optical sensor 10 is not limited to optical energy sources 12 which produce optical energy within the visible spectrum. While the preferred sensor 10 is shown with a LED serving as an optical energy source 12, other optical energy sources useful with the invention include lasers, laser diodes, incandescent bulbs, fluorescent bulbs, halogen bulbs or a combination of such sources. For particular applications, it may be preferable that the optical energy produced by the optical energy source be "monochromatic" in the sense that it is limited to one wavelength or a narrow bandwidth. The optical energy source may be modulated for particular applications. Reflectors, lenses or other optical components (not shown) may be added to alter the path of the optical energy between the fibers 16, 20 or the element 14.

Optical energy from the optical energy source 12 is directed into the element 14 by the optical fiber 16 at a specified angle $\theta_i$ relative to the normal 42 to the measuring surface 32. While the preferred means shown for light conduction is an optical fiber, other means such as a light pipe, a light guide or a gradient index lens may be used. As shown in FIG. 3, the optical fiber 16 is fixed near its end 40 at an angle $\theta_i$ with a normal 42 to the light-receiving surface 30 by means of an adhesive (not shown). Preferably, the refractive index of the adhesive is suitably matched to the indices of refraction of the element 14 and the optical fiber 16 to minimize distortion of the optical energy transmitted by the optical fiber 16.

The photodetector 18 receives and measures the intensity of optical energy reflected at the surface 32 or otherwise transmitted through the element 14 away from the measuring surface 32. Preferred photodetectors 18 include photodiodes and phototransistors, but may also include other types of detectors such as photomultipliers, charge coupled devices or a linear array of photodiodes. While the photodetector 18 is shown in FIG. 3 as coupled to the element 14 by means of the optical fiber 20, the photodetector 18 may also be secured directly to the element 14 with a suitable adhesive. Needless to say, the photodetector 18 should be sensitive to those wavelengths of optical energy reflected or otherwise transmitted through the element 14 away from the measuring surface 32 which form the basis for the optical sensing function.

In the embodiment shown in FIG. 3, the element 14 and the photodetector 18 are coupled by means of an optical fiber 20. While the preferred means shown for coupling the element 14 and the photodetector 18 is an optical fiber, other means such as a light pipe, a light guide or a gradient index lens may be used. An end 44 of the optical fiber 20 is positioned along the light-incident surface 30 of the element 14 so as to maximize the receipt of optical energy reflected at the measuring surface 32. To further maximize the receipt of reflected optical energy, the end 44 of the optical fiber 20 is oriented at an angle equal to $\theta_r$ relative to the normal 42 of the light-incident surface 30 of the element 14. As with the optical fiber 16, the optical fiber 20 is oriented near its end 44 at an angle such that the surface at the end 44 lies flat along the light-incident surface 30 when the central axis of the optical fiber 20 near the end 44 makes an angle equal to $\theta_i$ with a normal to the light receiving surface 30. The end 44 of the optical fiber 20 is fixed to the light-incident surface 30 by means of an adhesive (not shown) having an index of refraction suitably matched to minimize optical energy loss between the element 14 and the optical fiber 20.

When used in a refractometer, the measuring surface 32 is brought into contact with a sample 50. Optical energy from optical energy source 12 travels through the optical fiber 16. The optical energy exits the optical fiber 16 into the element 14 and is incident on the measuring surface 32 in the area of a sensing region 52. Optical energy incident on the sensing region 52 is partially transmitted into the sample 50 at its interface with the measuring surface 32 and is partially reflected back through the element 14 away from the measuring surface 32 towards the light-incident surface 30 and the optical fiber 20. Optical energy reflected at the sensing region 52 is conducted by the optical fiber 20 to the photodetector 18, the intensity of optical energy reflected onto photodetector 18 being a function of the refractive index of the sample 50 in contact with sensing region 52.

Because the refractive indices of many solutions are very temperature dependent, a thermistor 60 (FIG. 4) is required for temperature compensation. The thermistor or other thermal sensor is preferably located on or near the light-incident surface 30 of the element 14 to provide an accurate measure of the temperature of the sample 50.

Figure 4:
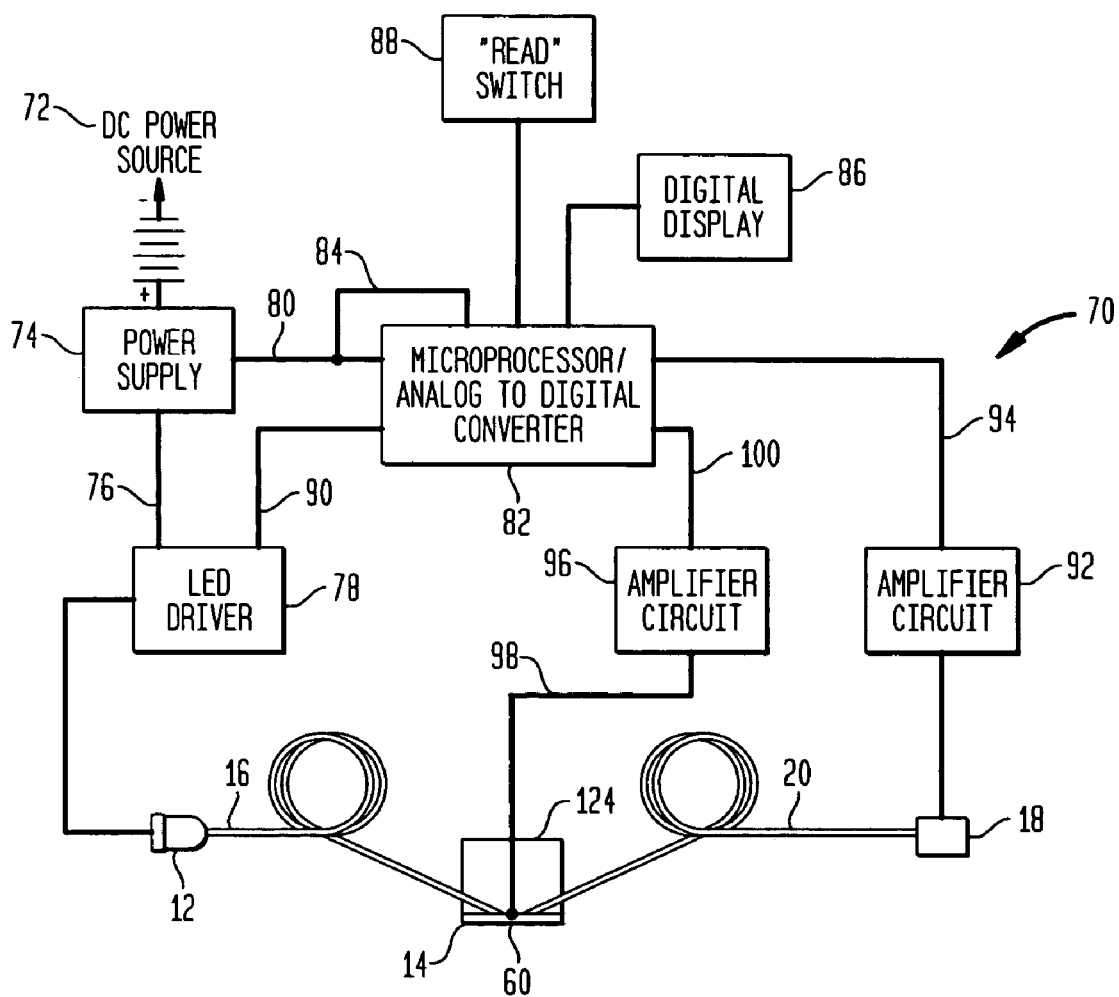
FIG. 4 is a schematic diagram of an electronic circuit for use in connection with the optical sensor of FIG. 3.

Electronic circuitry 70 for driving the optical sensor 10 as a refractometer is shown schematically in FIG. 4. A DC power source 72 (preferably a battery) provides power to a power supply 74. One analog power line 76 connects the power supply 74 with an LED driver 78, while another analog power line 80 connects the power supply 74 with a microprocessor 82. The voltage output by the power supply 74 is monitored by the microprocessor 82 on a line 84.

The microprocessor 82 communicates with the LED driver 78, the thermistor 60, photodetector 18, a digital display 86 and a "READ" switch 88. Line 90 connects the microprocessor 82 with the LED driver 78, which in turn is connected to the optical energy source (in the preferred mode, LED) 12. Amplifier circuit 92 receives the output from the photodetector 18 and relays the amplified output to the microprocessor 82 on the line 94. Similarly, amplifier circuit 96 receives the output from the thermistor 60 on the line 98 and relays the amplified output to the microprocessor 82 on the line 100. The lines 94 and 100 communicate with the microprocessor 82 through an analog-to-digital converter (not shown) which may be either internal or external to the microprocessor.

The LED driver 78 includes an amplifier supply and a current regulating circuit for supplying an adjustable supply current to the optical energy source 12. The preferred "READ" switch 88 is a push button switch of either the normally open or normally closed type depending on the signal characteristics of the microprocessor 82.

When a user presses the "READ" switch 88 the microprocessor 82 signals the LED driver 78 to pulse the optical energy source 12 through the line 90. The photodetector 18 generates a signal corresponding to the intensity of optical energy reflected at the measuring surface 32 which is amplified by the amplifier 92 and sent to the microprocessor 82 via the line 94. Additionally, the microprocessor 82 monitors the signal of the thermistor 60 which is amplified by the amplifier 96 and carried to the microprocessor by the line 100. The signals from the photodetector 18 and the thermistor 60 are digitized and the microprocessor 82 compensates for the temperature indicated by the thermistor 60. The microprocessor then displays a result corresponding to the desired units of measurement on the digital display 86. When the "READ" switch 88 is released, the microprocessor 82 resets the LED driver 78 to repeat the process of pulsing the optical energy source 12.

Figure 5:
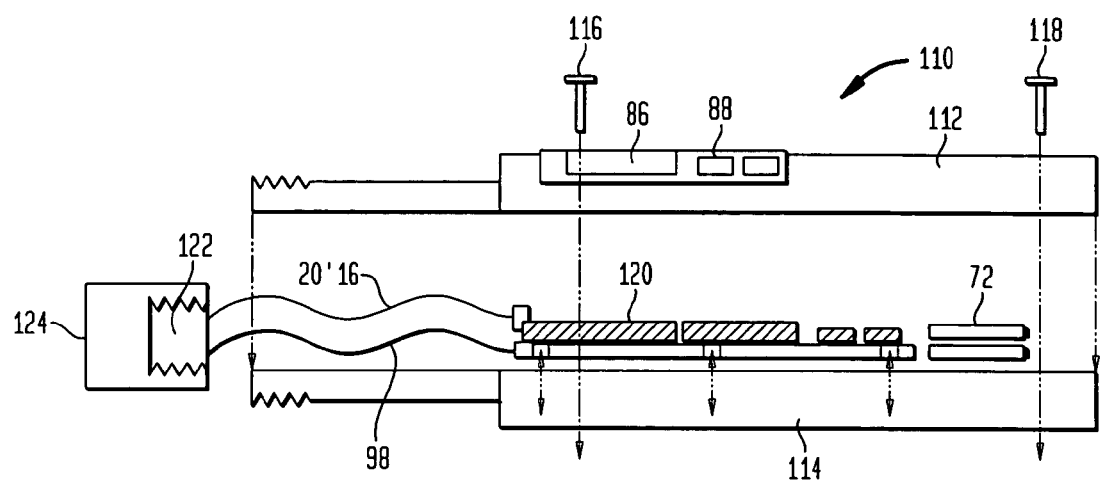
FIG. 5 is a schematic diagram of a probe-type instrument incorporating the optical sensor of FIG. 3.

A handheld probe-type instrument 110 incorporating the optical sensor 10 and the circuit 70 is shown schematically in FIG. 5. The instrument 110 includes a plastic enclosure in two halves 112, 114 held together by retaining screws 116, 118. These two halves 112, 114 sandwich the internal components of the instrument, including the power source 72 and a printed circuit board 120 for carrying the circuit 70. The digital display 86 and the "READ" switch 88 are mounted on the exterior of half 112. The element 14 and thermistor 60 are contained in a sensor housing or probe 122 in such manner that the measuring surface 32 of the element 14 is exposed at a distal end 124 of the sensor housing 122. The element 14 and thermistor 60 are secured to the printed circuit board 120 by fiber optics 12, 16 (only one shown) and electrical line 98. In practice, the distal end 124 of the probe 122 is exposed to a substance to be tested (not shown) and, when the "READ" switch 88 is pressed, the index of refraction of the substance appears on the digital display 86.

While the invention has been described in connection with several examples, modifications to those examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. A method for determining the concentration of a solute in a composition comprising the solute in a solvent, the method comprising the steps of:
    a) measuring the refractive index of a test composition having an unknown concentration of the solute in the solvent, wherein the composition is selected from the group consisting of:
        i) a paste having at least 5% weight percent solids of a vinyl ac'etate monomer, vinyl acetate oligomers, vinyl acetate polymers, or a combination thereof and a viscosity of at least 100 cps at 25° C.; and
        ii) an aqueous solution comprising polyvinyl alcohol;
    b) determining the concentration of the solute in the composition by correlating the refractive index of the test composition to a calibration table which relates refractive index to the solute concentration, wherein the calibration table was prepared by measuring the refractive index of a plurality of known compositions, each of the known compositions having a known solute concentration, wherein the components of the test composition are essentially identical to the components of the known compositions, and wherein the refractive index of the test composition and the refractive index of the known compositions is measured using a fiber optic refractometer.

2. The method according to claim 1, wherein the test composition is an aqueous solution comprising polyvinyl alcohol.

3. The method according to claim 2, wherein the aqueous solution comprising polyvinyl alcohol is prepared by dispersing particulate polyvinyl alcohol in water and cooking the mixture at a temperature between about 140° F. and 205° F. for at least about 20 minutes.

4. The method according to claim 2, wherein the test composition comprises a polyvinyl alcohol in which a 4% aqueous solution of the polyvinyl alcohol has a viscosity of from about 2 cps to about 10,000 cps at 20° C.

5. The method according to claim 2, wherein the test solution comprises about 4 percent to about 25 percent by weight polyvinyl alcohol resin.

6. A method of determining a solute concentration in a viscous paste sample having an unknown concentration of greater than 5 weight percent of a solute in a solvent, the method comprising:
    a) correlating refractive index with the solute concentration in the solvent at a particular temperature by measuring the refractive index of a plurality of standard solutions at a first temperature, each having a known solute concentration, including at least two standard solutions each having a concentration of the solute in the solvent of greater than about 5 weight percent, to produce a correlation at a first temperature;
    b) measuring the refractive index of the paste sample having an unknown solute concentration with a fiber optic refractometer probe at a second temperature; and
    c) determining the concentration of the solute in the sample by comparing the refractive index of the paste sample with the correlation of step (a).

7. The method according to claim 6, wherein the solvent comprises methanol.

8. The method according to claim 6, wherein the solvent comprises water.

9. The method according to claim 6, wherein the solute comprises vinyl acetate monomer.

10. The method according to claim 6, wherein the solute comprises vinyl acetate oligomers, vinyl acetate polymers, or a combination thereof.

11. The method of claim 6, wherein the paste sample has a solute concentration of at least about 20 weight percent.

12. The method of claim 6, wherein the paste sample has a solute concentration of at least about 30 weight percent.

13. The method of claim 6, wherein the paste sample has a solute concentration of at least about 40 weight percent.

14. The method according to claim 6, wherein the paste sample has a viscosity of at least 2500 cps.

15. The method according to claim 6, wherein the paste sample has a viscosity of at least 5000 cps.

16. The method according to claim 6, wherein the paste sample has a viscosity of at least 10,000 cps.

17. The method according to claim 6, wherein the paste sample has a viscosity of at least about 25,000 cps.

18. The method according to claim 6, wherein the paste sample has a viscosity of from about 50,000 cps to about 100,000 cps.

19. The method according to claim 6, wherein the paste sample has a viscosity of from about 65,000 cps to about 90,000 cps.

20. The method according to claim 6, wherein the step of correlating refractive index with the solute concentration in the solvent includes measuring the refractive index of at least two standard solutions with a fiber optic refractometer probe.

21. The method according to claim 20, wherein the two standard solutions each have a viscosity of from about 25,000 cps to about 100,000 cps.

22. The method according to claim 6, wherein the fiber optic refractometer probe is coupled to an optical energy source for supplying optical energy by way of a first optical fiber and the probe includes an element including a material transparent to at least a portion of such optical energy defining a planar light incident and a planar measuring surface; the first optical fiber connecting the optical energy source and the element for transmitting such optical energy through the element obliquely toward the measuring surface, the first optical fiber also being optically coupled to said element; and wherein the measuring surface is coupled to a photodetector communicating with the element by way of a second optical fiber in a line of reflection of such optical energy from the measuring surface for measuring a multitude of discrete changes in an intensity of optical energy transmitted through the element away from the measuring surface, and being operative to generate a signal that is a function of the measured changes in said intensity.

23. The method according to claim 22, wherein the fiber optic sensor includes a temperature sensor.

24. The method according to claim 23, wherein the first temperature is different from the second temperature by a temperature difference of about 10° C. to about 40° C.

25. The method according to claim 24, wherein the first temperature is from about 20° C. to about 30° C.

26. The method according to claim 25, wherein the second temperature is from about 30° C. to about 60° C.

27. The method according to claim 26, wherein the second temperature is from about 35° C. to about 40° C.

28. The method of claim 6, wherein the refractive index of the standard solutions, the refractive index of the paste sample, or both are measured by,
submersing the fiber optic refractometer probe into a sample and allowing it to equilibrate for a period of from about 30 seconds to about 20 minutes prior to measuring the refractive index of the sample.

29. The method according to claim 28, wherein the refractometer probe is allowed to equilibrate for at least about 1 minute prior to measuring the refractive index of the sample.

30. The method according to claim 28, wherein the refractometer probe is allowed to equilibrate for at least about 2 minutes prior to measuring the refractive index of the sample.

31. The method according to claim 28, wherein the refractometer probe is allowed to equilibrate for at least about 4 minutes prior to measuring the refractive index of the sample.

32. In a process for converting vinyl acetate to polyvinyl alcohol including the steps of measuring the concentration of a vinyl acetate paste and adjusting concentration of the paste in response to the measurement, the improvement comprising: determining the concentration of the vinyl acetate in the vinyl acetate paste according to the method of claim 1, and adjusting the concentration of the vinyl acetate paste in response to the determination of the concentration of the vinyl acetate in the vinyl acetate paste.

33. In a saponification process involving conversion of vinyl acetate to polyvinyl alcohol at an acid/caustic ratio, the improvement comprising: determining the concentration of the polyvinyl alcohol in the saponification process according to the method of claim 1, and adjusting the ratio of acid to caustic in response to the determination of the concentration of the polyvinyl alcohol in the saponification process.

* * * * *